(12) United States Patent
Bhatia

(10) Patent No.: US 8,778,424 B2
(45) Date of Patent: Jul. 15, 2014

(54) COMPOSITIONS AND METHODS FOR TREATING HAIR LOSS

(76) Inventor: Tasneem Bhatia, Atlanta, GA (US)

( * ) Notice: Subject to any disclaimer, the term of this patent is extended or adjusted under 35 U.S.C. 154(b) by 75 days.

(21) Appl. No.: 13/342,920

(22) Filed: Jan. 3, 2012

(65) Prior Publication Data

US 2013/0017285 A1 Jan. 17, 2013

Related U.S. Application Data

(60) Provisional application No. 61/429,212, filed on Jan. 3, 2011.

(51) Int. Cl.
*A61K 36/00* (2006.01)

(52) U.S. Cl.
USPC .................. 424/777; 424/779; 424/725

(58) Field of Classification Search
None
See application file for complete search history.

(56) References Cited

U.S. PATENT DOCUMENTS

| 6,013,279 A * | 1/2000 | Klett-Loch | 424/451 |
| 2009/0110674 A1 * | 4/2009 | Loizou | 424/94.2 |

FOREIGN PATENT DOCUMENTS

WO     WO 9505146 A1 * 2/1995

\* cited by examiner

*Primary Examiner* — Chris R Tate
*Assistant Examiner* — Deborah Davis
(74) *Attorney, Agent, or Firm* — Meunier Carlin & Curfman LLC

(57) ABSTRACT

Provided are compositions containing a unique combination of vitamin B1, vitamin B6, vitamin B12, folic acid, magnesium glycinate, ferric glycinate, L cysteine, biotin, *Polygonum multiflorum*, and *Emblica officinalis*. Methods of increasing hair volume in a subject by administering to the subject a composition containing vitamin B1, vitamin B6, vitamin B12, folic acid, magnesium glycinate, ferric glycinate, L cysteine, biotin, *Polygonum multiflorum*, and *Emblica officinalis* are also included.

19 Claims, No Drawings

COMPOSITIONS AND METHODS FOR TREATING HAIR LOSS

CROSS-REFERENCE TO RELATED APPLICATIONS

This application claims the priority benefit of U.S. Provisional Patent Application No. 61/429,212 filed Jan. 3, 2011.

FIELD OF THE INVENTION

This invention relates to compositions and methods for treating hair loss. More particularly, the present invention describes compositions and methods for arresting hair loss and/or promoting hair growth.

BACKGROUND OF THE INVENTION

All human hair goes through normal cycles of growth and rest. These phases are termed anagen, catagen, and telogen and they differ in length for different hair types. The growth phase, or anagen phase, in scalp hair lasts between two and eight years whereas the anagen phase in eyebrow hair lasts approximately four to seven months. Differences in the length of the anagen phase result in different hair lengths.

During the anagen phase, cell division at the base of the hair follicle adds cells to the hair shaft and results in hair growth. Hair grows approximately one centimeter, or half an inch, a month. Scalp hair can stay in this active phase of growth for up to seven years, but on average, lasts two to three years. The amount of time the hair follicle stays in the anagen phase is genetically determined.

The anagen phase is followed by a brief two to four week catagen phase or transitional phase. This is part of a renewal process wherein the scalp follicle is degraded and the hair stops growing but does not fall out. The hair follicle shrinks to about ⅙ of the normal length during the catagen phase and a "club hair" is formed.

The scalp follicle then goes into the telogen phase for two to four months. The telogen phase is also called the resting phase. During the telogen phase, the scalp hair still does not grow but remains attached to the follicle. Approximately ten to fifteen percent of all scalp hairs are in this phase at any one time. After the telogen phase, the cycle is complete and the hair follicle goes back into the anagen phase. Formation of the new hair shaft causes the old hair to be pushed out and lost. On average, 50-100 scalp hairs are lost due to this natural growth process every day.

Hair loss only becomes problematic when the rate of shedding exceeds the rate of regrowth or when new hair is thinner than the hair shed. A shift in the balance of hair loss and hair regrowth can be caused by many factors. Pattern baldness, or androgenetic alopecia, is likely caused by hereditary factors. Scarring on the scalp caused by inflammation can cause excessive hair loss as can poor nutrition, radiation, chemotherapy, medications, disease, hormonal changes, hair treatments, emotional distress, and sudden or excessive weight loss.

Treatments for baldness and excessive hair loss have been developed. Topical minoxidil and oral finasteride both treat male pattern baldness. A synthetic substance, anthralin, is also used by some doctors to treat cases of alopecia areata, a hair loss condition believed to be associated with autoimmune disease. Corticosteroids may also be injected into the scalp to treat certain types of excessive hair loss.

Despite the many advances in hair loss treatment, these prior treatments are either chemical or hormonal in nature. Adverse side effects such as severe allergic reactions, chest pain, unexplained weight gain, fainting, swollen hands and feet, decreased libido, and erectile dysfunction are associated with many of the hair loss treatments currently available. Accordingly, there remains a need for more natural and effective compositions for the treatment of hair loss.

SUMMARY OF THE INVENTION

The present invention answers the need for compositions that are natural and effective for the treatment of hair loss. These compositions are effective for increasing hair volume. An increase in hair volume encompasses a reduction of hair shedding, an increase in hair growth, an increase in hair shaft diameter, and/or an improvement in hair tension.

Provided are compositions containing a unique combination of vitamin B1, vitamin B6, vitamin B12, folic acid, magnesium glycinate, ferric glycinate, L cysteine, biotin, *Polygonum multiflorum*, and *Emblica officinalis*. The present invention further includes methods of increasing hair volume in a subject by administering to the subject a composition containing vitamin B1, vitamin B6, vitamin B12, folic acid, magnesium glycinate, ferric glycinate, L cysteine, biotin, *Polygonum multiflorum*, and *Emblica officinalis*.

DETAILED DESCRIPTION OF THE INVENTION

The present invention provides hair treatment compositions comprising vitamin B1, vitamin B6, vitamin B12, folic acid, magnesium glycinate, ferric glycinate, L cysteine, biotin, *Polygonum multiflorum*, and *Emblica officinalis*. The present invention further provides hair treatments consisting essentially of vitamin B1, vitamin B6, vitamin B12, folic acid, magnesium glycinate, ferric glycinate, L cysteine, biotin, *Polygonum multiflorum*, and *Emblica officinalis*, *Polygonum multiflorum* is also referred to as He Shou Wu, whereas *Emblica officinalis* is also referred to as Indian gooseberry. These compositions are effective and natural treatments for increasing hair volume in a subject. The term "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the term "vitamin B1" includes thiamin hydrochloride, thiamin pyrophosphate (TPP), thiamin monophosphate (TMP), and thiamin diphosphate (TDP). In a preferred embodiment, the vitamin B1 is thiamin hydrochloride. The term "vitamin B6" includes pyridoxine hydrochloride and pyridoxal 5'-phosphate (PLP). In a preferred embodiment, the vitamin B6 is pyridoxine hydrochloride. The term "vitamin B12" includes methylcobalamin, cyanocobalamin, hydroxycobalamin, and adenosylocobalamin. In a preferred embodiment, the vitamin B12 is methylcobalamin.

In one embodiment of the present invention, the hair treatment composition comprises vitamin B1 in an amount of about 10 mg to about 40 mg. In another embodiment, the hair treatment composition comprises vitamin B6 in an amount of about 10 mg to about 40 mg. In another embodiment, the hair treatment composition comprises vitamin B12 in an amount of about 500 μg to about 1500 μg. In another embodiment, the hair treatment composition comprises folic acid in an amount of about 400 μg to about 1200 μg. In another embodiment, the hair treatment composition comprises magnesium glycinate in an amount of about 100 mg to about 300 mg. In another embodiment, the hair treatment composition comprises L cysteine in an amount of about 30 mg to about 90 mg. In another embodiment, the hair treatment composition comprises biotin in an amount of about 2500 μg to about 7500 μg. In another embodiment, the hair treatment composition comprises ferric glycinate in an amount of about 7 mg to about 25 mg.

In another embodiment, the hair treatment composition comprises *Polygonum multiflorum* in an amount of about 250 mg to about 750 mg. The *Polygonum multiflorum* is preferably a powder or ground substance derived from a dried *Polygonum multiflorum* plant part or parts. In other embodiments, the *Polygonum multiflorum* is a liquid extract of a *Polygonum multiflorum* plant part or parts. The *Polygonum multiflorum* can be derived from any part, or combination of parts, of the *Polygonum multiflorum* plant, including but not limited to, the root, leaf, fruit, flower, vine, and stalk. In a preferred embodiment, the *Polygonum multiflorum* is derived from the root, and more preferably is a dried *Polygonum multiflorum* root in particulate form. The term "particulate" refers to powders, granular substances and the like.

In another embodiment, the hair treatment composition comprises *Emblica officinalis* in an amount of about 250 mg to about 750 mg. The *Emblica officinalis* is preferably a powder or ground substance derived from a dried *Emblica officinalis* tree part or parts. In other embodiments, the *Emblica officinalis* is a liquid extract of an *Emblica officinalis* tree part or parts. The *Emblica officinalis* can be derived from any part, or combination of parts, of the *Emblica officinalis* tree, including but not limited to, the root, leaf, fruit, bark, and flower. In a preferred embodiment, the *Emblica officinalis* is powder or ground substance derived from a dried fruit, and more preferably a berry.

In a preferred embodiment, the hair treatment composition comprises a combination of vitamin B1, vitamin B6, vitamin B12, folic acid, magnesium glycinate, L cysteine, biotin, ferric glycinate, *Polygonum multiflorum*, and *Emblica officinalis* wherein the amounts of one or more of those components is as follows: about 10 mg to about 40 mg of vitamin B1, about 10 mg to about 40 mg of vitamin B6, about 500 μg to about 1500 μg of vitamin B12, about 400 μg to about 1200 μg of folic acid, about 100 mg to about 300 mg of magnesium glycinate, about 30 mg to about 90 mg of L cysteine, about 2500 μg to about 7500 μg of biotin, about 7 mg to about 25 mg of ferric glycinate, about 250 mg to about 750 mg of *Polygonum multiflorum*, and about 250 mg to about 750 mg of *Emblica officinalis*. Hair treatment compositions for administration to pregnant or breastfeeding women will preferably contain about 10 mg to about 40 mg of vitamin B1, about 10 mg to about 40 mg of vitamin B6, about 500 μg to about 1500 μg of vitamin B12, about 400 μg to about 1200 μg of folic acid, about 100 mg to about 300 mg of magnesium glycinate, about 30 mg to about 90 mg of L cysteine, about 2500 μg to about 7500 μg of biotin, and about 7 mg to about 25 mg of ferric glycinate, but will not contain *Polygonum multiflorum* or *Emblica officinalis*.

In other embodiments of the present invention, the hair treatment composition comprises about 25 mg of vitamin B1. In another embodiment, the hair treatment composition comprises about 25 mg of vitamin B6. In another embodiment, the hair treatment composition about 1000 μg of vitamin B12. In another embodiment, the hair treatment composition comprises about 800 μg of folic acid. In another embodiment, the hair treatment composition comprises about 200 mg of magnesium glycinate. In another embodiment, the hair treatment composition comprises about 60 mg of L cysteine. In another embodiment, the hair treatment composition comprises about 5000 μg of biotin. In another embodiment, the hair treatment composition comprises about 15 mg of ferric glycinate. In another embodiment, the hair treatment composition comprises about 500 mg of *Polygonum multiflorum*. In another embodiment, the hair treatment composition comprises about 500 mg of *Emblica officinalis*.

In a further preferred embodiment, the hair treatment composition comprises a combination of vitamin B1, vitamin B6, vitamin B12, folic acid, magnesium glycinate, L cysteine, biotin, ferric glycinate, *Polygonum multiflorum*, and *Emblica officinalis* wherein the amounts of one or more of those components is as follows: about 25 mg of vitamin B1, about 25 mg of vitamin B6, about 1000 μg of vitamin B12, about 800 μg of folic acid, about 200 mg of magnesium glycinate, about 60 mg of L cysteine, about 5000 μg of biotin, about 15 mg of ferric glycinate, about 500 mg of *Polygonum multiflorum*, and about 500 mg of *Emblica officinalis*. Hair treatment compositions for administration to pregnant or breastfeeding women will preferably contain about 25 mg of vitamin B1, about 25 mg of vitamin B6, about 1000 μg of vitamin B12, about 800 μg of folic acid, about 200 mg of magnesium glycinate, about 60 mg of L cysteine, about 5000 μg of biotin, and about 15 mg of ferric glycinate, but will not contain *Polygonum multiflorum* or *Emblica officinalis*.

The hair treatment compositions of the present invention may be formulated in any of a variety of suitable forms, for example, oral, topical or parenteral administration. Standard pharmaceutical formulation techniques known by those of skill in the art may be used to prepare these formulations. Depending upon the particular route of administration, a variety of carriers well known in the art may be used. These include solid or liquid fillers, diluents, hydrotropes, surface-active agents and encapsulating substances. Optional pharmaceutically active or cosmetically active materials may be included which do not substantially interfere with the activity of the hair treatment compositions used in the methods of the present invention. The amount of carrier employed in conjunction with the hair treatment compositions used in the methods of the present invention is sufficient to provide a practical quantity of material for administration per unit dose of the compositions.

The term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques. Typically, the hair treatment compositions of the present invention are administered orally. Various oral dosage forms can be used, including such solid forms as tablets, capsules, granules and bulk powders. These oral forms comprise an effective amount of a hair treatment composition. In a preferred embodiment, a hair treatment composition is administered as a tablet. As used herein, the term "hair treatment composition" includes one or more tablets or capsules as ingested daily such that the milligram amounts provided herein are daily intake amounts. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents and melting agents.

Orally administered hair treatment compositions also include liquid solutions, emulsions, suspensions, powders, granules, elixirs, tinctures, syrups and the like. The carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, Avicel RC-591, tragacanth and sodium alginate; typical wetting agents include lecithin and polysorbate 80; and typical preservatives include methyl paraben and sodium benzoate. Peroral liquid hair treatment compositions may also contain one or more components such as sweeteners, flavoring agents or colorants as described above. Liquid oral dosage forms also include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

Other formulations useful for attaining systemic delivery of the hair treatment compositions of the present invention include sublingual, buccal and nasal dosage forms. Such hair treatment compositions typically comprise one or more soluble filler substances such as sucrose, sorbitol and mannitol; and binders such as acacia, microcrystalline cellulose, carboxymethyl cellulose and hydroxypropyl methylcellulose. Glidants, lubricants, sweeteners, colorants, antioxidants and flavoring agents described above may also be included.

The hair treatment compositions of the present invention can also be applied topically. The carrier of a topical hair treatment composition may aid penetration of the composition into the skin to reach the environment of the hair follicle. Such topical hair treatment compositions may be in any form including, for example, solutions, oils, creams, ointments, gels, lotions, pastes, shampoos, leave-on and rinse-out hair conditioners, milks, cleansers, moisturizers, sprays, aerosols, skin patches and the like. A variety of carrier materials well known in the art for topical application, such as, for example, water, alcohols, aloe vera gel, allantoin, glycerine, vitamin A and E oils, mineral oil, propylene glycol, and the like can be used to prepare such formulations.

Topical formulations are often prepared in the form of emulsions. The term "emulsion," as used herein refers to mixtures of two or more liquids, which may be in the form of a continuous phase and a disperse phase, for example. Exemplary emulsions may be in the form of creams, lotions, ointments, gels, etc. and may include, for example, oil-in-water emulsions, water-in-oil emulsions, multiple emulsions and microemulsions. These formulations will be prepared which contain from about 0.001 to 10 w/w % of the hair treatment compositions of the present invention. These formulations will then be applied to the desired areas from 1 to 4 times daily. Alternatively, these formulations will be applied to the desired areas less frequently, i.e., from 1 to 5 times a week.

The hair treatment compositions may also be administered topically in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. A potential formulation for topical delivery of the hair treatment compositions used in the methods of the present invention utilizes liposomes such as described in U.S. Pat. No. 4,911,928 and U.S. Pat. No. 5,834,014.

Carriers for systemic administration include, for example, sugars, starches, cellulose and its derivatives, malt, gelatin, talc, calcium sulfate, vegetable oils, synthetic oils, polyols, alginic acid, phosphate buffer solutions, emulsifiers, isotonic saline and pyrogen-free water. Suitable carriers for parenteral administration include, for example, propylene glycol, ethyl oleate, pyrrolidone, ethanol, and sesame oil.

The formulations described above can be used in the methods of the present invention. The present invention includes methods of increasing hair volume in a mammal comprising administering a hair treatment composition to the mammal, wherein the composition comprises vitamin B1, vitamin B6, vitamin B12, folic acid, magnesium glycinate, ferric glycinate, L cysteine, biotin, *Polygonum multiflorum*, and *Emblica officinalis*. As used herein, the term "increasing hair volume" includes, but is not limited to, a reduction of hair shedding, an increase in hair growth, an increase in hair shaft diameter (also referred to herein as hair coarseness), an improvement in hair tension, and any combination thereof. In a preferred embodiment, the hair is scalp hair and the hair treatment composition is administered orally. In a further preferred embodiment, the composition is in the form of a tablet and is administered at least one to two times a day for approximately one, two, three, four or more months.

In one embodiment of the present invention, hair volume is increased in a mammal by administering to the mammal a hair treatment composition that comprises vitamin B1 in an amount of about 10 mg to about 40 mg. In another embodiment, hair volume is increased in a mammal by administering to the mammal a hair treatment composition that comprises vitamin B6 in an amount of about 10 mg to about 40 mg. In another embodiment, hair volume is increased in a mammal by administering to the mammal a hair treatment composition that comprises vitamin B12 in an amount of about 500 µg to about 1500 µg. In another embodiment, hair volume is increased in a mammal by administering to the mammal a hair treatment composition that comprises folic acid in an amount of about 400 µg to about 1200 µg. In another embodiment, hair volume is increased in a mammal by administering to the mammal a hair treatment composition that comprises magnesium glycinate in an amount of about 100 mg to about 300 mg. In another embodiment, hair volume is increased in a mammal by administering to the mammal a hair treatment composition that comprises L cysteine in an amount of about 30 mg to about 90 mg. In another embodiment, hair volume is increased in a mammal by administering to the mammal a hair treatment composition that comprises biotin in an amount of about 2500 µg to about 7500 µg. In another embodiment, hair volume is increased in a mammal by administering to the mammal a hair treatment composition that comprises ferric glycinate in an amount of about 7 mg to about 25 mg. In another embodiment, hair volume is increased in a mammal by administering to the mammal a hair treatment composition that comprises *Polygonum multiflorum* in an amount of about 250 mg to about 750 mg. In another embodiment, hair volume is increased in a mammal by administering to the mammal a hair treatment composition that comprises *Emblica officinalis* in an amount of about 250 mg to about 750 mg.

In a preferred embodiment, hair volume is increased in a mammal by administering to the mammal a hair treatment composition that comprises a combination of vitamin B1, vitamin B6, vitamin B12, folic acid, magnesium glycinate, L cysteine, biotin, ferric glycinate, *Polygonum multiflorum*, and *Emblica officinalis* wherein the amounts of one or more of those components is as follows: about 10 mg to about 40 mg of vitamin B1, about 10 mg to about 40 mg of vitamin B6, about 500 µg to about 1500 µg of vitamin B12, about 400 µg to about 1200 µg of folic acid, about 100 mg to about 300 mg of magnesium glycinate, about 30 mg to about 90 mg of L cysteine, about 2500 µg to about 7500 µg of biotin, about 7 mg to about 25 mg of ferric glycinate, about 250 mg to about 750 mg of *Polygonum multiflorum*, and about 250 mg to about 750 mg of *Emblica officinalis*.

In other embodiments of the present invention, hair volume is increased in a mammal by administering to the mammal a hair treatment composition that comprises about 25 mg of vitamin B1. In another embodiment, hair volume is increased in a mammal by administering to the mammal a hair treatment composition that comprises about 25 mg of vitamin B6. In another embodiment, hair volume is increased in a mammal by administering to the mammal a hair treatment composition that comprises about 1000 µg of vitamin B12. In another embodiment, hair volume is increased in a mammal by administering to the mammal a hair treatment composition that comprises about 800 µg of folic acid. In another embodiment, hair volume is increased in a mammal by administering to the mammal a hair treatment composition that comprises about 200 mg of magnesium glycinate. In another embodiment, hair volume is increased in a mammal by administering to the mammal a hair treatment composition that comprises about 60 mg of L cysteine. In another embodiment, hair volume is increased in a mammal by administering to the mammal a hair treatment composition that comprises about 5000 µg of biotin. In another embodiment, hair volume is increased in a mammal by administering to the mammal a hair treatment composition that comprises about 15 mg of ferric glycinate. In another embodiment, hair volume is increased in a mammal by administering to the mammal a hair treatment composition that comprises about 500 mg of *Polygonum multiflorum*. In another embodiment, hair volume is increased in a mammal by administering to the mammal a hair treatment composition that comprises about 500 mg of *Emblica officinalis*.

In a further preferred embodiment, hair volume is increased in a mammal by administering to the mammal a hair treatment composition that comprises a combination of vitamin B1, vitamin B6, vitamin B12, folic acid, magnesium glycinate, L cysteine, biotin and ferric glycinate wherein the amounts of one or more of those components is as follows: about 25 mg of vitamin B1, about 25 mg of vitamin B6, about 1000 µg of vitamin B12, about 800 µg of folic acid, about 200 mg of magnesium glycinate, about 60 mg of L cysteine, about 5000 µg of biotin, about 15 mg of ferric glycinate, about 500 mg of *Polygonum multiflorum*, and about 500 mg of *Emblica officinalis*.

EXAMPLE

The compositions and methods provided herein will be further understood by reference to the following non-limiting example.

Treatment of Patients Resulting in Decreased Hair Loss, Increased Hair Growth and/or Increased Hair Diameter Five human patients were treated with a tablet composition comprising about 25 mg of vitamin B1, about 25 mg of vitamin B6, about 1000 µg of vitamin B12, about 800 µg of folic acid, about 200 mg of magnesium glycinate, about 60 mg of L cysteine, about 5000 µg of biotin, about 15 mg of ferric glycinate, about 500 mg of *Polygonum multiflorum*, and about 500 mg of *Emblica officinalis*. Each patient displayed hair thinning or excessive hair shedding prior to treatment. Patients were treated daily (via self-administration) for four months with the following results:

Patient 1 presented with diffuse alopecia or adrogenetic alopecia. Following four months of daily treatment with the above-described composition, Patient 1 showed new hair growth in the vertex region of the scalp, increased hair diameter and decreased hair loss.

Patient 2 presented with excessive hair shedding. Following four months of daily treatment with the above-described composition, Patient 2 showed decreased hair loss.

Patient 3 presented with regions of hair thinning. Following four months of daily treatment with the above-described composition, Patient 3 showed evidence of new hair growth at the temple region of the scalp.

Patient 4 presented with fine, limp hair. Patient 4 had course thick hair before the hair transitioned to a fine, limp hair. Following four months of daily treatment with the above-described composition, Patient 4 showed an increase in the number of course, thick hairs.

Patient 5 presented with excessive hair shedding. Following four months of daily treatment with the above-described composition, Patient 5 showed decreased shedding of hair.

It is understood that the examples and embodiments described herein are for illustrative purposes only and that various modifications or changes in light thereof will be suggested to person skilled in the art and are to be included with the spirit and purview of this applications and scope of the appended claims. All publications, patents and patent applications cited herein are hereby incorporated by reference in their entirety for all purposes.

What is claimed is:

1. A composition for increasing hair volume consisting essentially of about 10 mg to about 40 mg of vitamin B1, about 10 mg to about 40 mg of vitamin B6, about 500 µg to about 1500 µg of vitamin B12, about 400 µg to about 1200 µg of folic acid, about 100 mg to about 300 mg of magnesium glycinate, about 30 mg to about 90 mg of L cysteine, about 2500 µg to about 7500 µg of biotin, about 7 mg to about 25 mg of ferric glycinate, about 250 mg to about 750 mg of *Polygonum multiflorum*, and about 250 mg to about 750 mg of *Emblica officinalis*, and optionally, a carrier.

2. The composition of claim 1, wherein the composition comprises about 25 mg of vitamin B1, about 25 mg of vitamin B6, about 1000 µg of vitamin B12, about 800 µg of folic acid, about 200 mg of magnesium glycinate, about 60 mg of L cysteine, about 5000 µg of biotin, about 15 mg of ferric glycinate, about 500 mg of *Polygonum multiflorum*, and about 500 mg of *Emblica officinalis*.

3. The composition of claim 1, wherein the *Polygonum multiflorum* is a dried *Polygonum multiflorum* root in particulate form.

4. The composition of claim 1, wherein the *Emblica officinalis* is a dried *Emblica officinalis* berry in particulate form.

5. The composition of claim 1, wherein the *Polygonum multiflorum* is a dried *Polygonum multiflorum* root in particulate form and the *Emblica officinalis* is a dried *Emblica officinalis* berry in particulate form.

6. The composition of claim 1, where the composition is a tablet.

7. A method of increasing hair volume in a subject comprising administering to the subject a composition consisting essentially of about 10 mg to about 40 mg of vitamin B1, about 10 mg to about 40 mg of vitamin B6, about 500 µg to about 1500 µg of vitamin B12, about 400 µg to about 1200 µg of folic acid, about 100 mg to about 300 mg of magnesium glycinate, about 30 mg to about 90 mg of L cysteine, about 2500 µg to about 7500 µg of biotin, about 7 mg to about 25 mg of ferric glycinate, about 250 mg to about 750 mg of *Polygonum multiflorum*, and about 250 mg to about 750 mg of *Emblica officinalis* and optionally, a carrier.

8. The method of claim 7, wherein the composition comprises about 25 mg of vitamin B1, about 25 mg of vitamin B6, about 1000 μg of vitamin B12, about 800 μg of folic acid, about 200 mg of magnesium glycinate, about 60 mg of L cysteine, about 5000 μg of biotin, about 15 mg of ferric glycinate, about 500 mg of *Polygonum multiflorum* and about 500 mg of *Emblica officinalis*.

9. The method of claim 7, wherein the *Polygonum multiflorum* is a dried *Polygonum multiflorum* root in particulate form.

10. The method of claim 7, wherein the *Emblica officinalis* is a dried *Emblica officinalis* berry in particulate form.

11. The method of claim 7, wherein the composition is an emulsion.

12. The method of claim 7, wherein the hair is scalp hair.

13. The method of claim 7, wherein the subject is a human.

14. The method of claim 13, wherein the human is treated for at least four months.

15. The method of claim 7, wherein the composition is a tablet that is administered orally at least once daily.

16. The method of claim 14, wherein the composition is administered once daily.

17. The method of claim 7, wherein hair shedding is reduced.

18. The method of claim 7, wherein hair growth is increased.

19. The method of claim 7, wherein hair shaft diameter is increased.

* * * * *